United States Patent [19]

Collins et al.

[11] Patent Number: 4,572,163

[45] Date of Patent: Feb. 25, 1986

[54] VALVE BODY FOR ENDOSCOPE

[75] Inventors: Ian P. Collins, Welwyn; William J. Revell, Great Dunmow, both of England

[73] Assignee: Warner-Lambert Technologies, Inc., Dallas, Tex.

[21] Appl. No.: 670,860

[22] Filed: Nov. 13, 1984

[30] Foreign Application Priority Data

Dec. 11, 1983 [GB] United Kingdom ............... 8330240

[51] Int. Cl.⁴ .............................................. A61B 1/06
[52] U.S. Cl. ...................................... 128/4; 251/337; 251/322
[58] Field of Search ................... 128/4, 6, 7; 251/337, 251/336, 321, 322, 324

[56] References Cited

U.S. PATENT DOCUMENTS

| | | | |
|---|---|---|---|
| 3,958,566 | 5/1976 | Furihata | 128/4 |
| 4,261,343 | 4/1981 | Ouchi et al. | 128/4 |
| 4,311,134 | 1/1982 | Mitsui et al. | 128/6 |
| 4,325,362 | 4/1982 | Ouchi et al. | 128/4 |
| 4,469,090 | 9/1984 | Konomura | 128/4 |

*Primary Examiner*—William H. Grieb
*Attorney, Agent, or Firm*—Alan H. Spencer

[57] ABSTRACT

A valve body (20) for an endoscope is moulded from polypropylene and has a straight through bore (27) to aid cleaning of the valve body. The valve body (20) has spaced external ribs (48, 50) which locate the valve body (20) with respect to the casing of a handle (10) of the endoscope. At one end the valve body (20) receives a threaded sleeve (30) which retains a slidable valve member (34) in position, a cap (42) being manually depressed against spring loading to open the valve and place a source of suction in communication with a side stem (38) which is intended to be connected to a passageway leading to the distal end of the endoscope shaft.

9 Claims, 5 Drawing Figures

VALVE BODY FOR ENDOSCOPE

DESCRIPTION

FIELD OF THE INVENTION

This invention relates to valve bodies for endoscopes, which are medical instruments for inspecting the cavities of internal organs.

BACKGROUND TO THE INVENTION

A typical form of known endoscope has a handle from which extends a flexible shaft terminating in a distal or operative end which is inserted into a cavity to be inspected. To enable the shaft to reach inaccessible locations, and to be capable of controlled adjusting movement, the shaft is flexible and incorporates wires which are pulled in a controlled way as a result of manual adjustment of remote knobs or wheels on the endoscope handle. Light is also transmitted through the shaft between the handle and the distal end of the shaft, to enable the cavity to be inspected. It is also usual to provide two tubes extending between the handle and the distal end of the shaft, one for leading air and water to the distal end of the shaft, and one for biopsy and suction.

The application of suction is controlled by means of a value on the handle. The valve is connected to adjacent tubing by soldered connections, and the internal passages defined by this arrangement are complex in shape and virtually impossible to clean thoroughly. It will be realised that body fluids are sucked through these passages and the ability to clean them effectively is highly desirable.

An object of the invention is to provide a valve body for an endoscope, the valve body being readily cleaned and of a simpler and cheaper construction than the prior soldered arrangement.

SUMMARY OF THE INVENTION

According to one aspect of the invention a valve body for an endoscope is moulded from a synthetic plastics material and has a straight through bore with a side port, one end of the through bore being open to receive a valve member which is slidable in the bore to control communication between the other end of the bore and the side port, and the valve body having spaced formations on respective sides of the side port for locating the valve body with respect to a casing of the endoscope, whereby when the valve body is fitted to the casing the valve body extends completely therethrough.

Since the through bore is straight, and the valve body is arranged to extend completely through the casing, the valve can be very readily cleaned by removing the valve member and gaining access to the through bore from said one end thereof.

The valve member is preferably retained in position in the through bore by means of a sleeve which is threaded into said one end of the through bore and which can be unscrewed therefrom to release the valve member for cleaning of the through bore. A return spring may be located between the valve member and the sleeve in order to urge the valve member towards a closed position in which there is no communication between the other end of the bore and the side port. To open the valve, the valve member is moved against its spring loading to place the other end of the bore in communication with the side port, this action simultaneously blocking off the end of a central passage in the valve member through which suction is applied when the valve is in its closed position.

The valve body is conveniently moulded from polypropylene, and said formations are conveniently external ribs on the exterior of the valve body, these ribs locating against the casing where the valve body emerges therefrom. One of said ribs may be elliptical to locate the valve body against a curved region of the endoscope casing. The other rib is preferably annular and is arranged to locate and retain the valve body against the casing with the aid of a spring clip, allowing a certain degree of tolerance or play.

According to another aspect of the invention an endoscope has a valve for controlling the application of suction at the distal end of a shaft of the endoscope, the valve being mounted in a handle casing of the endoscope and comprising a valve body moulded from a synthetic plastics material and having a straight through bore with a side port communicating with a passage in the shaft to apply suction at the distal end of the shaft, a valve member slidable in the bore between an open position in which suction applied to the bore is communicated to the side port and a closed position in which the side port is not in communication with the other end of the bore, the valve body extending completely through the casing so that at one end of the body the valve member, or an element attached thereto, is accessible for manual movement of the valve member, and at the other end of the valve body the valve body is accessible outside the casing for attachment to a source of suction.

The invention will now be further described by way of example with reference to the accompanying drawings in which:

FIG. 1 is a fragmentary perspective view showing an endoscope handle cut away to reveal the valve body fitted therein, the valve body being in accordance with the invention, FIG. 2 is a perspective view, partially cut away, showing the valve member with its associated valve components, FIG. 3 is a side elevation of the valve body, FIG. 4 is a sectional view on the line IV—IV of FIG. 3, and FIG. 5 is an end view of the valve body.

DETAILED DESCRIPTION OF THE DRAWINGS

Figure 1:
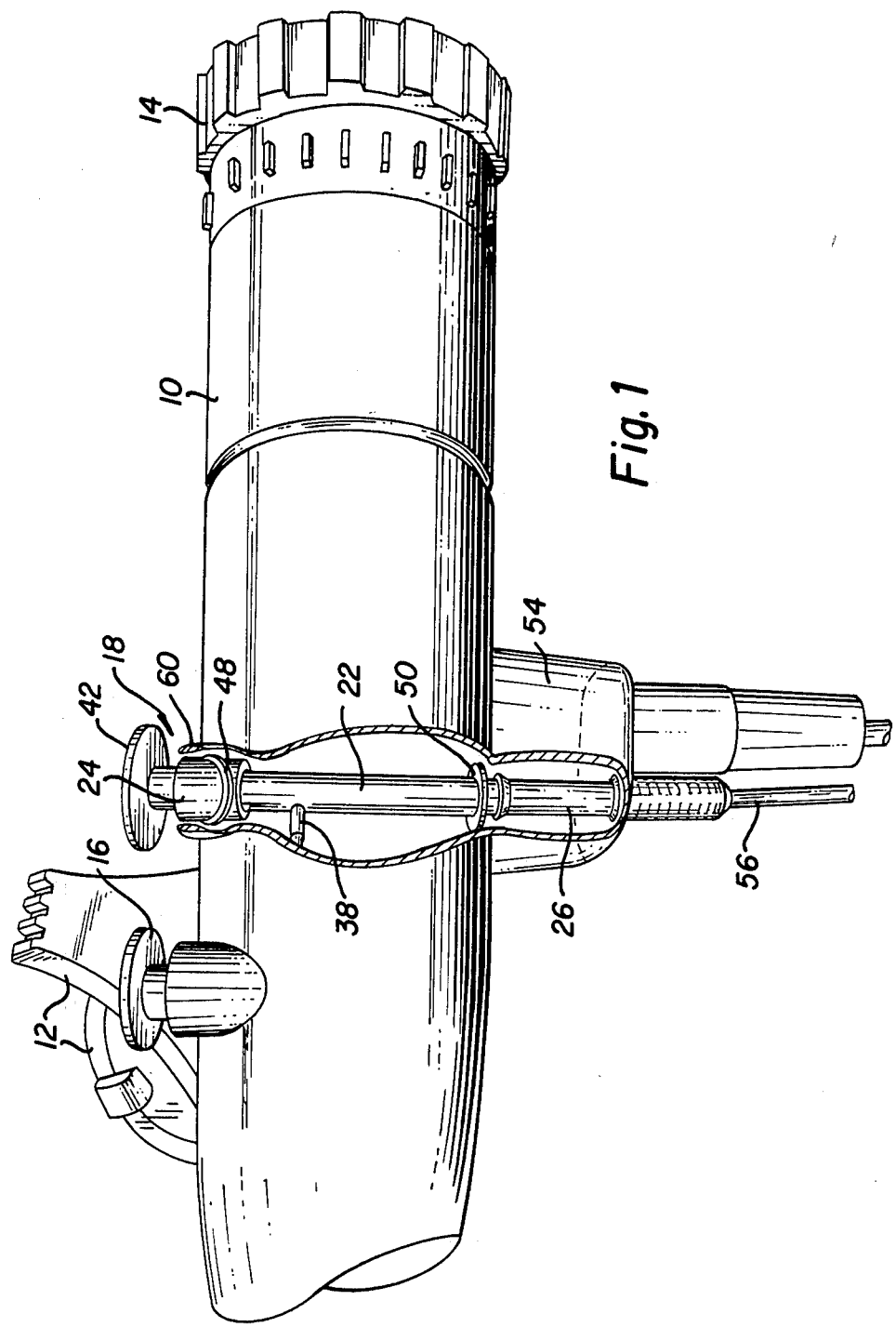

FIG. 1 shows the handle 10 of an endoscope which has a flexible shaft (not shown) extending from the left hand end of the handle 10. The handle 10 has control knobs 12 for controlling flexing movement of the shaft, and an adjustment ring 14 for focusing the image transmitted to the handle 10 from the distal end of the endoscope shaft. In addition, the handle 10 has a manually operable check valve 16 for controlling the supply of fluid to the distal end of the shaft, and a suction valve 18 for controlling the application of suction to the distal end of the shaft. The following description is concerned mainly with the construction of the suction valve 18 because the invention lies in the construction of this valve and, in particular the body of the valve 18.

Figure 2:
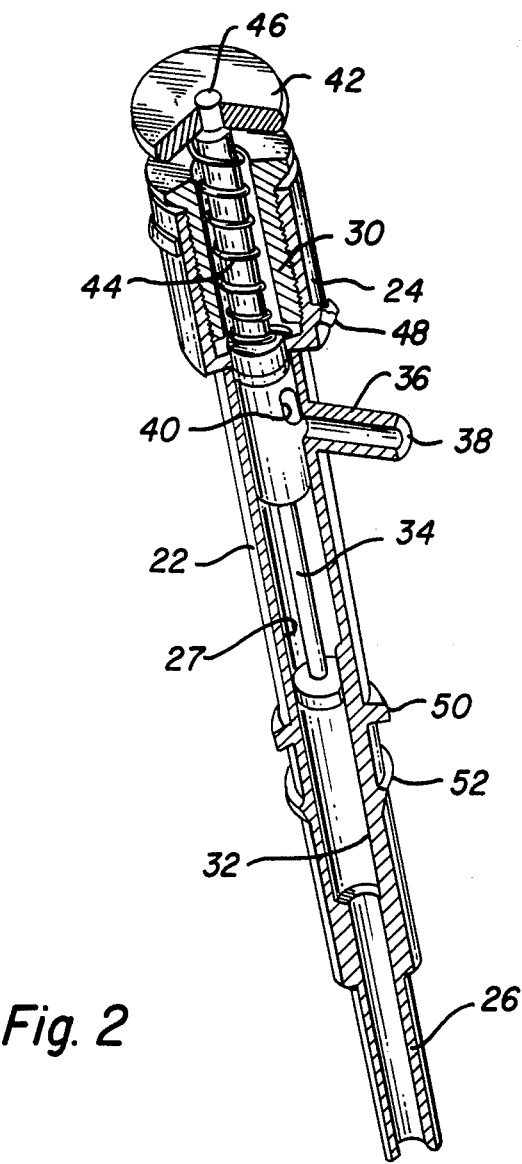

Referring particularly to FIGS. 1 and 2, the valve body is shown at 20 and is in the form of a component moulded from polypropylene. The valve body 20 has a main portion 22 of generally cylindrical shape which at one end of the valve body adjoins an enlarged head 24 and at the other end of the valve body adjoins a reduced diameter stem 26.

Figure 4:
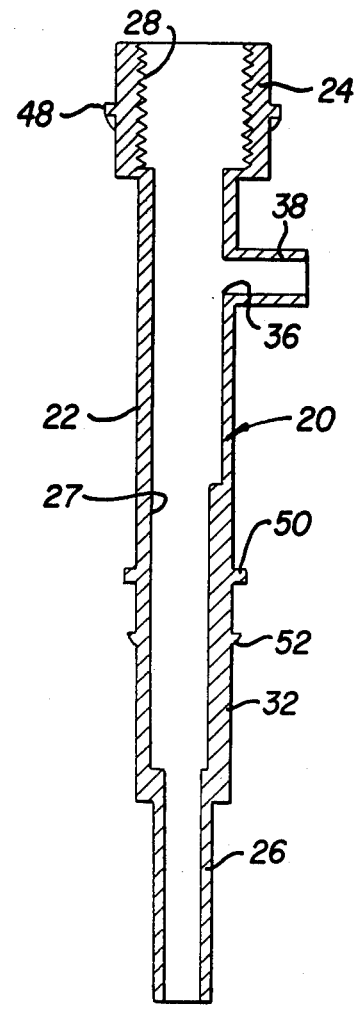
Figure 5:
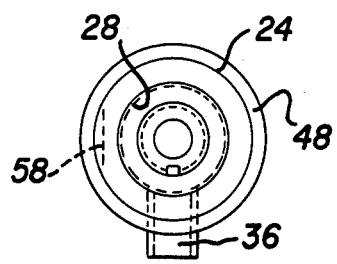

A straight through bore 27 extends completely through the valve body 20. As best shown in FIG. 4, this through bore 27 has an enlarged threaded counterbore 28 in the head 24, and this threaded counterbore receives a threaded sleeve 30 (FIG. 2). Within the main portion 22 of the valve body 20, the through bore 27 is cylindrical, except for a longitudinally extending rib 32 which is provided to guide longitudinal sliding movement of a valve member 34 (FIG. 2). The lower end of the valve member is slotted to cooperate with the rib 32. The main body portion 22 of the valve body 20 also has a side port 36 leading to an integrally moulded side stem 38.

The valve member 34 has a longitudinally extending passage therethrough, this passage communicating with a port 40 in the side wall of the valve member 34. The upper end of the valve member 34, as viewed in FIG. 2, has affixed thereto a cap 42, and a helical compression spring 44 acts between this cap 42 and the sleeve 30 to urge the valve member 34 to the closed position in which the side port 40 is not in communication with the side port 36. Hence, when the valve is in the open position shown in FIG. 2 suction applied to the stem 26 is in communication with the atmosphere through the hole 46 in the centre of the cap 42. When the cap 42 is manually depressed against the bias of the spring 44, the valve member 34 moves within the valve body to place the side ports 40 and 36 in communication, thereby applying suction to the side stem 38 and thence through the endoscope shaft to the operative distal end thereof.

As can be seen from FIG. 1, the valve body 20 extends completely through the casing of the handle 10. The head 24 of the valve body 20 has an external elliptical rib 48 which locates that end of the valve body against the curved portion of the casing of the handle 10. Where the valve body 20 emerges from the handle 10, the valve body 20 has an external annular rib 50 adjacent a smaller shoulder 52. A spring clip (not shown) is located between the annular rib 50 and the shoulder 52 to locate and retain that portion of the valve body where it emerges from the handle 10, the arrangement of the spaced rib 50, shoulder 52 and spring clip providing a certain degree of tolerance or play. The stem 26 passes through a rubber boot 54 and has connected thereto a tube 56 leading to the source of suction. It will be appreciated that the side stem 38, which is located within the handle 10, is connected by tubing to passageways in the endoscope shaft leading to the distal end thereof.

Figure 3:
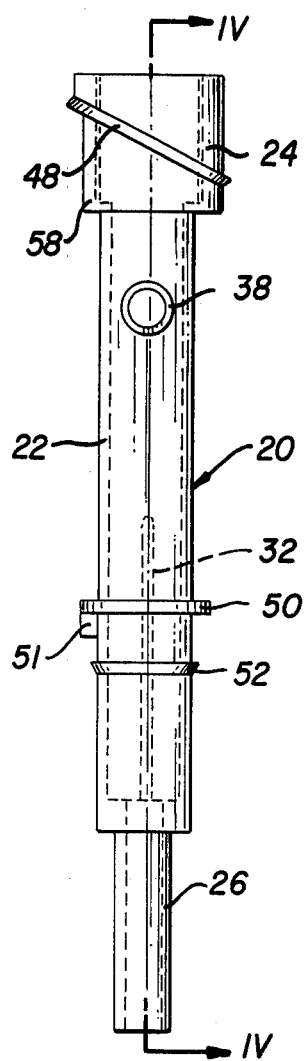

To prevent unwanted rotation of the valve body 20 within the casing of the handle 10, the rib 50 has a pip 51 (FIG. 3). The head 24 of the body 20 has a chordal flat 58 to provide clearance for an adjacent part.

Because the valve body extends completely through the handle 10, and because the through bore 27 in the body 20 is straight, cleaning of the valve is simple and effective. This is done by unscrewing the sleeve 30, withdrawing the valve member 34 from the through bore 27 and cleaning the latter. The valve member 34 can be cleaned separately and then the valve components reassembled.

We claim:

1. A valve body for an endoscope, the body being moulded from a synthetic plastics material and having a straight through bore with a side port, one end of the through bore being open to receive a valve member which is slidable in the bore to control communication between the other end of the bore and the side port, and the valve body having spaced formations on respective sides of the side port for locating the valve body with respect to a casing of the endoscope, whereby when the valve body is fitted to the casing the valve body extends completely therethrough.

2. A valve body according to claim 1, wherein said formations are external ribs on the exterior of the valve body.

3. A valve body according to claim 2, wherein one of said ribs is elliptical to locate the valve body against a curved region of the endoscope casing, and the other rib is annular and is arranged to locate and retain the valve body against the casing with the aid of a spring clip, allowing a certain degree of tolerance or play.

4. A valve body according to claim 3 and moulded from polypropylene.

5. A valve body according to claim 3, wherein said one end of the valve body has a threaded counterbore to receive a sleeve for retaining a slidable valve member in the valve body.

6. An endoscope having a valve for controlling the application of suction at the distal end of a shaft of the endoscope, the valve being mounted in a handle casing of the endoscope and comprising a valve body moulded from a synthetic plastics material and having a straight through bore with a side port communicating with a passage in the shaft to apply suction at the distal end of the shaft, a valve member slidable in the bore between an open position in which suction applied to the bore is communicated to the side port and a closed position in which the side port is not in communication with the bore, the valve body extending completely through the casing so that at one end of the body the valve member, or an element attached thereto, is accessible for manual movement of the valve member, and at the other end of the valve body the valve body is accessible outside the casing for attachment to a source of suction.

7. An endoscope according to claim 6, wherein said one end of the valve body in counterbored and receives a threaded sleeve which can be unscrewed to release the valve member for cleaning of the through bore.

8. An endoscope according to claim 7, wherein a return spring is located between the valve member and the sleeve in order to urge the valve member towards the closed position in which there is no communication between the other end of the bore and the side port.

9. An endoscope according to claim 8, wherein to open the valve the valve member is moved against its spring loading to place the other end of the bore in communication with the side port, this action simultaneously blocking off the end of a central passage in the valve member through which suction is applied when the valve is in its closed position.

* * * * *